United States Patent [19]

Symon et al.

[11] 4,313,002

[45] Jan. 26, 1982

[54] PREPARATION OF P-AMINODIPHENYLAMINES

[75] Inventors: Ted Symon, Lombard; Paul R. Kurek, Schaumburg; Michael D. Tufano, Broadview, all of Ill.

[73] Assignee: UOP Inc., Des Plaines, Ill.

[21] Appl. No.: 201,846

[22] Filed: Oct. 29, 1980

[51] Int. Cl.³ .................... C07C 85/11; C07C 85/24; C07C 85/26
[52] U.S. Cl. .................... 564/423; 564/410; 564/421; 564/422; 564/437
[58] Field of Search ............... 564/423, 422, 421, 410

[56] References Cited

U.S. PATENT DOCUMENTS

| | | | |
|---|---|---|---|
| 2,974,169 | 3/1961 | Newby et al. ............ | 564/423 X |
| 3,728,392 | 4/1973 | Levy ........................ | 564/410 |
| 3,729,512 | 4/1973 | L'Eplattenier et al. ..... | 564/423 |

FOREIGN PATENT DOCUMENTS

| | | | |
|---|---|---|---|
| 37-7222 | 7/1962 | Japan ...................... | 564/423 |
| 935303 | 8/1963 | United Kingdom ......... | 564/423 |
| 947082 | 1/1964 | United Kingdom ......... | 564/423 |

OTHER PUBLICATIONS

Augustine, "Catalytic Hydrogenation," p. 95 (1965).

Primary Examiner—John Doll
Attorney, Agent, or Firm—James R. Hoatson, Jr.; Eugene I. Snyder; William H. Page, II

[57] ABSTRACT

A method of preparing p-aminodiphenylamines from diphenylamines is described whereby neither the N-nitrosodiphenylamine or the p-nitrosodiphenylamine need be isolated. The method rests on the discovery that alkali metal salts of p-nitrosodiphenylamines are soluble in non-aqueous organic solvent systems consisting of certain aromatic hydrocarbons and saturated aliphatic alcohols, and that such salts can be readily hydrogenated in their non-aqueous solution to the corresponding p-aminodiphenylamine.

22 Claims, No Drawings

PREPARATION OF P-AMINODIPHENYLAMINES

BACKGROUND OF THE INVENTION p-Aminodiphenylamines are widely used as intermediates in the manufacture of alkylated derivatives, which find broad utility as antiozonants and antioxidants. For example, reductive alkylation of p-aminodiphenylamine (PADPA) with acetone provides the broadly used antiozonant N-phenyl-N'-isopropyl-p-phenylenediamine.

The most accessible route to p-aminodiphenylamines involves N-nitrosation of a diphenylamine, rearrangement of the resulting N-nitrosodiphenylamine (NNODPA) to the corresponding C-nitrosodiphenylamine, or p-nitrosodiphenylamine (PNODPA), and subsequent hydrogenation of the latter to the p-aminodiphenylamine. It has long been known that the procedure is fraught with difficulties, some of which result from objectionable properties of p-nitrosodiphenylamine, which is representative of the class of C-nitrosodiphenylamines. In particular, the latter are carcinogens requiring extensive precautions in their handling, which problem is compounded by the fact that p-nitrosodiphenylamine is often obtained as a light powder, easily dispersed and airborne. Another difficulty arises from the thermal instability of p-nitrosodiphenylamines, so that there is a tendency during their subsequent hydrogenation toward formation of highly-colored by-products which are difficult to remove from PADPA and which substantially reduce the commercial value of the latter material.

U.S. Pat. No. 2,974,169 describes the reduction of an aqueous solution of an alkaline metal salt of PNODPA with palladium on charcoal. This method has the advantage of obviating, in large part, the formation of objectionable color bodies. However, reduction in aqueous media presents substantial disadvantages, and because the reference contemplates isolation of PNODPA the necessity of handling carcinogens remains.

The discovery leading to this invention is that certain metal salts of p-nitrosodiphenylamines are soluble in particular organic solvents. Such solubility makes possible the preparation of p-aminodiphenylamines from their corresponding diphenylamine without the necessity of isolating and handling the p-nitrosodiphenylamine.

SUMMARY OF THE INVENTION

The object of this invention is to prepare p-aminodiphenylamines from diphenylamines without the necessity of isolating p-nitrosodiphenylamines as intermediates. An embodiment of this invention comprises nitrosating a diphenylamine, rearranging the resulting N-nitrosodiphenylamine in a non-aqueous organic solvent with a mineral acid to form the p-nitrosodiphenylamine or its mineral acid salt, converting the p-nitrosodiphenylamine to an alkali metal salt so as to form a non-aqueous phase containing said alkali metal salt, hydrogenating the non-aqueous phase, and recovering the formed p-aminodiphenylamine. In a more specific embodiment the non-aqueous organic solvent is a water insoluble saturated aliphatic alcohol containing up to about 10 carbon atoms, or consists essentially of approximately equal quantities by weight of an aromatic hydrocarbon with a boiling point from about 80° to about 160° C. and a saturated aliphatic alcohol containing up to about 10 carbon atoms. In a still more specific embodiment the aromatic hydrocarbon is benzene and the alcohol is 1-butanol. In yet another embodiment the aromatic hydrocarbon is toluene and the alcohol is selected from the group consisting of methanol, 1-butanol, and 1-hexanol. In still another embodiment, the hydrogenation catalyst is palladium.

It is to be understood that p-nitrosodiphenylamine is but one member of the class of C-nitrosodiarylamines, and when used herein reference is made to the entire such class. Similarly, N-nitrosodiphenylamine is viewed as but representative of the class of N-nitrosodiarylamines, and p-aminodiphenylamine is representative of the class of p-aminodiarylamines.

DESCRIPTION OF THE INVENTION

Because of the toxicity of N-nitrosodiphenylamine and its rearrangement product, p-nitrosodiphenylamine, their use in the preparation of p-aminodiphenylamine is fraught with hazards. A preparation of PNODPA without isolating NNODPA is described in U.S. Pat. No. 3,728,392, which is incorporated herein by reference. This application describes the preparation of PADPA directly from diphenylamine in high yield and good purity by a method which obviates the necessity of isolating, and thereby handling, either NNODPA or PNODPA. The invention is based on the discovery that alkali metal salts of PNODPA are soluble in non-aqueous solvents such as water insoluble saturated aliphatic alcohols or mixtures of aromatic compounds and aliphatic alcohols, and that hydrogenation of non-aqueous solutions of these salts in said solvents leads to PADPA. Even when the alkali metal salt is insoluble in an organic solvent, the resulting suspension may be hydrogenated to afford PADPA, but not necessarily with equivalent results.

Although the method described herein is especially applicable to the preparation of p-aminodiphenylamine because of its commercial importance, the method is broadly applicable to the class of p-aminodiphenylamines. Thus, it is to be understood that this method is applicable to diphenylamines substituted on one or more rings with alkyl, alkoxy, and halogen, to cite but a few possible substituents. Examples of suitable diphenylamines include 2-alkoxy, 2,2'-dialkoxy and 2,4'-dialkoxydiphenylamines, where the alkoxy group may be methoxy, ethoxy, propoxy, butoxy, pentoxy, and so on, and corresponding phenoxy and benzyloxy analogs, similarly substituted halodiphenylamines, where the halogen may be fluorine, chlorine, bromine, or iodine, and 2-alkyl, 2,2'- and 2,4'-dialkyldiphenylamines, where the alkyl group may be methyl, ethyl, propyl, butyl, pentyl, hexyl, decyl, hexadecyl, and so forth.

Briefly described, the invention comprises nitrosating a diphenylamine to form a N-nitrosodiphenylamine, rearranging the N-nitrosodiphenylamine in a non-aqueous organic solvent by contacting the resulting non-aqueous solution with from about 1 to about 5 molar proportions of a mineral acid so as to form the p-nitrosodiphenylamine or its mineral acid salt in the non-aqueous organic solvent, converting the p-nitrosodiphenylamine to its alkali metal salt by addition of an aqueous solution of an alkali metal base, hydrogenating the non-aqueous phase in the presence of hydrogen and an effective amount of a hydrogenation catalyst, and recovering the p-aminodiphenylamine formed thereby.

Among the organic solvents which may be used in this invention are aliphatic and aromatic hydrocarbons, saturated aliphatic alcohols and ethers, glycols such as ethylene glycol and polyethylene glycol, monoethers of the glycols, and combinations thereof. An essential limitation upon the organic solvents is that they be unreactive under the conditions of the described process.

Nitrosation of the p-aminodiphenylamine may be effected by conventional means, as exemplified in U.S. Pat. No. 3,728,392. Alternately, nitrosation of the diphenylamine may be effected in non-aqueous organic media, such as water insoluble saturated aliphatic alcohols or mixtures of aromatic compounds and aliphatic alcohols.

Rearrangement of the N-nitrosodiphenylamine to p-nitrosodiphenylamine is effected by contacting the solution of the N-nitrosodiphenylamine with mineral acid. Hydrogen halides are commonly used, and hydrogen chloride is preferred. The hydrogen halide may be used in from about 1 to about 5 molar proportions, based on the diphenylamine, with the range of 1.2 to about 1.8 being somewhat preferred. Generally, the rearrangement is carried out at a temperature under about 70° C.

Where the N-nitrosodiphenylamine is prepared by conventional methods, it is first dissolved in an aromatic solvent whose boiling point is between about 80° and about 160° C. Examples of such solvents include benzene, toluene, ethylbenzene, and the xylenes. Thereafter the hydrocarbon solution containing the NNODPA is mixed with a solution of the hydrogen halide in a saturated aliphatic alcohol containing up to about 10 carbon atoms. A limitation on the alcohol is that it not be tertiary. Examples of such alcohols include methanol, ethanol, the propanols, the butanols, pentanols, hexanol, heptanols, octanols, nonanols, and decanols. Preferred alcohols in this variant include 1-butanol, 1-hexanol and 2-ethylhexanol. Generally, about equal weights of the aromatic compound and the aliphatic alcohol are used, although this is not critical.

Where the N-nitrosodiphenylamine is prepared in a non-aqueous solution, formation of the N-nitrosodiphenylamine and its rearrangement to the p-nitrosodiphenylamine occur concurrently. Typically, to a solution of the diphenylamine in an aromatic solvent, as described above, is added sodium nitrite followed by a solution of the hydrogen halide in a saturated aliphatic alcohol. Enough hydrogen halide is present to provide from about 2 to about 5 molar proportions based on diphenylamine. Approximately equal amounts by weight of the aromatic solvent and the aliphatic alcohol are used, although this is not critical. Among the preferred alcohols, which are saturated aliphatic alcohols, containing up to about 10 carbon atoms, as previously described, are methanol, 1-butanol, 1-hexanol, and 2-ethylhexanol.

In both of the variants described above, the saturated aliphatic alcohol may be replaced by a saturated aliphatic ether, where the aliphatic portion corresponds to that of the previously described alcohols, by ethylene or polyethylene glycol, or by aliphatic monoethers of said glycols whose aliphatic portion is that of the aforementioned alcohols.

In yet another variant of this process where formation of NNODPA and its rearrangement to PNODPA occur concurrently, a suspension of the diphenylamine and sodium nitrite in a water insoluble aliphatic alcohol is treated, as described above, with a solution of the hydrogen halide in an alcohol of this class. The water insoluble alcohol, by which is meant its solubility in water is less than about 15% at 20° C., must not be tertiary and is a saturated aliphatic alcohol containing up to about 10 carbon atoms, examples of which include the butanols, pentanols, hexanols, heptanols, octanols, nonanols, and decanols. Preferred alcohols include 1-butanol, 1-hexanol, and 2-ethylhexanol.

The next step in this process is the conversion of the rearrangement product to its alkali metal salt. The p-nitrosodiphenylamine is present after rearrangement at least in part as its mineral acid salt. The mixture is then contacted with an aqueous solution of a base of an alkali metal. Examples of suitable bases include the hydroxides and carbonates of lithium, sodium, potassium, cesium, and rubidium. The concentration of the alkali metal base may be up to about 25% by weight, but normally it is in the range from about 5 to about 20% by weight. The amount of base employed is equivalent to about 0.5 to about 1.5 molar proportions in excess of the amount of hydrogen halide used for rearrangement. For example, if 3 molar proportions of hydrogen halide is used in the rearrangement, then from 3.5 to about 4.5 molar proportions of base is used. This is necessary to neutralize the excess acid, convert the salt of p-nitrosodiphenylamine to its free base, and then convert the free base to its alkali metal salt.

Because the alkali metal salt of p-nitrosodiphenylamines is soluble in the organic solvent system used, at this stage there is present a two-phase system with the non-aqueous phase consisting largely of an alkali metal salt of a p-nitrosodiphenylamine dissolved in the non-aqueous organic solvent and an aqueous organic phase consisting largely of inorganic salts dissolved in water.

The ultimate step in this process is the hydrogenation of the non-aqueous organic phase which consists largely of the alkali metal salt of p-nitrosodiphenylamine. Hydrogenation may be conducted at pressures up to about 5000 psig, and generally pressures up to 1000 psig are sufficient. Hydrogenation temperatures may range up to about 200° C. Depending upon the catalyst used and the pressure employed, temperatures less than about 150° C. generally suffice and often may be less than about 100° C. Hydrogenation may be conducted either in a batch or continuous mode. Where the alkali metal salt of PNODPA is incompletely soluble in the organic solvent system, practical considerations limit the process to a batch mode.

Virtually any hydrogenation catalyst serves to effectuate the desired reduction. Examples of suitable catalysts include palladium, platinum, nickel, rhenium, rhodium, ruthenium, and copper chromite. Such catalysts may be used either unsupported or supported. If supported, they may be used on such supports as charcoal, keiselguhr, alumina, silica, and the like, although charcoal and keiselguhr are somewhat preferred. Where palladium or platinum is used, they may be used in amounts up to about 1% by weight, although they are generally present at less than about 0.1%, with the preferred range being 0.001 to about 0.01%. Where nickel is used, amounts may be up to about 10% but are generally less than about 1% with a preferred range of 0.05 to about 0.5%.

Although virtually all the alkali metal salt of the p-nitrosodiphenylamine is in the non-aqueous phase, it is not necessary to separate the non-aqueous phase prior to hydrogenation. Because trace amounts of the salt in the aqueous phase present pollution and health hazards, it may be advantageous to subject those phases to hydrogenation, thereby conferring environmental benefits to the waste water from the process. This is not an essential part of this invention, but nonetheless is one of the possible benefits accruing therefrom.

The following examples are merely illustrative and are not intended to limit this invention thereto.

EXAMPLE 1

Diphenylamine (169 g, 1 mole) was converted to p-nitrosodiphenylamine according to U.S. Pat. No. 3,728,392 using approximately equal amounts of toluene and 1-butanol as the solvent system. Upon neutralization of the p-nitrosodiphenylamine hydrochloride, the aqueous layer was separated and sufficient aqueous sodium hydroxide was added to convert the p-nitrosodiphenylamine to its sodium salt. The organic layer was separated and transferred to a 2-liter stirred autoclave. To this was added 10 g of 1 wt. % palladium on charcoal, and hydrogenation was conducted at 50° to 60° C. at 400 psig hydrogen. When hydrogenation was complete, as indicated by no further absorption of hydrogen, the catalyst was removed by filtration and the product was analyzed by high pressure liquid chromatography, which indicated an overall yield of p-aminodiphenylamine of 93%.

EXAMPLE 2

Diphenylamine (85 g 0.5 mol) was converted to p-nitrosodiphenylamine essentially as described above, except that instead of first neutralizing the hydrochloride and separating the aqueous layer, excess sodium hydroxide was immediately added to form the p-nitrosodiphenylamine sodium salt. Both aqueous and organic phases were hydrogenated at 50° to 60° C. under 400 to 500 psig hydrogen in the presence of 15 g of 1 wt. % palladium on charcoal catalyst. After the reaction was complete, catalyst was removed by filtration, solvents were removed by distillation, and a portion of the residue was distilled to afford an overall yield of p-aminodiphenylamine of 93.5%.

EXAMPLE 3

In this example the sodium salt of p-nitrosodiphenylamine was hydrogenated in a continuous manner over a fixed bed of catalyst. Diphenylamine (338 g, 2 mols) was converted to the sodium salt of p-nitrosodiphenylamine as in Example 2. A solution of approximately equal weights of toluene and 1-butanol was added to dilute the solution of the sodium salt to a concentration of about 13.5 wt. %, and enough water was added to dissolve all the inorganic salts present in the aqueous phase. The two phases were separated and simultaneously pumped into a tube reactor over a 0.4 wt. % palladium on charcoal catalyst at 125° C., 1000 psig hydrogen pressure at 1 liquid hourly space velocity based on total liquid. Thin layer chromatography indicated 100% conversion of p-nitrosodiphenylamine. Distillation of the residue after separation of the aqueous phase and removal of the organic solvents gave 95% p-aminodiphenylamine exclusive of losses from column hold-up.

EXAMPLE 4

To a 3-liter 4-neck flask equipped with a stirrer, dropping funnel, thermometer, water condenser and gas bubbler was charged 174 g (1.03 mol) diphenylamine, 450 g water and 52 g (0.52 mol) sulfuric acid (98%). The mixture was heated to 65° C. with good mixing. While maintaining the temperature at 65°–70° C., 72.5 g (1.05 mol) of sodium nitrite dissolved in 170 g of water was added over a period of about 1 hour. Stirring was continued for an additional 30 minutes. The mixture was cooled to about 25°–30° C., 200 g toluene was added to dissolve the N-nitrosodiphenylamine, and the toluene layer was separated and dried by azeotropically distilling out the water. The mixture was cooled to 25°–30° C. and added over a period of 1 hour to a cooled solution of 48 g (1.3 mol) anhydrous hydrogen chloride dissolved in 200 g n-hexanol. Separation of a dark red, crystalline precipitate commenced after about 15–20 minutes and continued throughout the addition. The slurry was then stirred for about 4 hours at about 35° C., after which the reaction is terminated by the addition, with vigorous stirring, of a solution of 100 g (2.5 mol) sodium hydroxide in 300 g, of water keeping the temperature below 50° C. The reaction mixture separated quickly into two layers upon stopping the stirring, with the sodium salt of p-nitrosodiphenylamine dissolved in the organic phase. The aqueous phase was removed, the organic phase was charged to a 1-liter stirred autoclave and hydrogenated at 50°–60° C. under 400 psig hydrogen in the presence of 10 g 1% palladium on charcoal catalyst. After about 2 hours the hydrogen take-up ceased, the reaction mixture was filtered to remove the catalyst, transferred to a separatory funnel, the alkaline aqueous phase was removed and the organic phase was washed with two 200 ml portions of water. Upon removal of the solvents, a dark grey solid of essentially pure p-aminodiphenylamine is recovered representing about 93% yield.

EXAMPLE 5

To a 2-liter 3-neck flask equipped with a stirrer, thermometer and dropping funnel was charged 85 g (0.05 mol) diphenylamine, 100 g toluene, 2 g water and 37 g (0.55 mol) sodium nitrite. The mixture was stirred and to it was added, over a period of about 1 hour, below the surface a cooled, previously prepared solution of 62 g (1.6 mol) anhydrous hydrogen chloride dissolved in 200 g n-butanol, keeping the temperature at 20°–30° C. After the addition of the acid, the mixture had a deep red, almost black color. The mixture was stirred for 4 hours during which the color gradually turned to an orange-red.

The reaction was terminated and the sodium salt of p-nitrosodiphenylamine was formed by the addition of 62 g (1.55 mol) sodium hydroxide dissolved in 186 g water. The whole reaction mixture, both organic and aqueous phases, were transferred to a 1-liter stirred autoclave and hydrogenated at 50°–60° C. under 450 psig hydrogen in the presence of 15 g 1% palladium on charcoal catalyst. After about 2 hours the reaction was completed, the contents were removed from the autoclave and the catalyst removed by filtration. The organic phase was separated from the aqueous phase and the solvents were removed by distillation. The residue was then distilled under high vacuum to give a tan solid with an overall yield of 91%.

What is claimed is:

1. A method of converting a p-nitrosodiphenylamine to a p-aminodiphenylamine comprising contacting a solution of an alkali metal salt of said p-nitrosodiphenylamine in a non-aqueous organic solvent with hydrogen in the presence of an effective amount of a hydrogenation catalyst under hydrogenation conditions, said solvent being a mixture of an aromatic hydrocarbon having a boiling point from about 80° to about 160° C. and a saturated aliphatic alcohol containing up to about 10 carbon atoms, and recovering said p-aminodiphenylamine.

2. The method of claim 1 wherein said solvent comprises approximately equal amounts by weight of said alcohol and said aromatic hydrocarbon.

3. The method of claim 1 where the aromatic hydrocarbon is selected from the group consisting of benzene, toluene, ethylbenzene, and the xylenes.

4. The method of claim 3 where the aromatic hydrocarbon is toluene.

5. The method of claim 3 where the aromatic hydrocarbon is benzene.

6. The method of claim 1 wherein said alcohol is 1-butanol.

7. The method of claim 1 wherein said alcohol is 1-hexanol.

8. The method of claim 1 wherein said alcohol is 2-ethylhexanol.

9. The method of claim 1 wherein the alcohol is methanol.

10. The method of claim 1 wherein the hydrogenation catalyst is selected from the group consisting of palladium, platinum, nickel, rhenium, rhodium, ruthenium, and copper chromite.

11. The method of claim 10 where the catalyst is palladium.

12. A method of preparing p-aminodiphenylamines comprising:
   (a) nitrosating a diphenylamine to form a N-nitrosodiphenylamine;
   (b) rearranging a solution of the N-nitrosodiphenylamine in a non-aqueous organic solvent by contacting the solution with from about 1 to about 5 molar proportions of a mineral acid so as to form the p-nitrosodiphenylamine or its mineral acid salt in the non-aqueous solvent, said solvent being a mixture of an aromatic hydrocarbon having a boiling point from about 80° to about 160° C. and a saturated aliphatic alcohol containing up to about 10 carbon atoms;
   (c) converting the p-nitrosodiphenylamine to its alkali metal salt in a non-aqueous phase by addition of from about 0.5 to about 1.5 molar proportions of an aqueous solution of an alkali metal base;
   (d) hydrogenating the non-aqueous phase of step (c) in the presence of hydrogen and an effective amount of a hydrogenation catalyst under hydrogenation conditions, and recovering the p-aminodiphenylamine formed thereby.

13. The method of claim 12 wherein the aromatic hydrocarbon is selected from the group consisting of benzene, toluene, ethylbenzene, and the xylenes.

14. The method of claim 13 where the aromatic hydrocarbon is toluene.

15. The method of claim 13 where the aromatic hydrocarbon is benzene.

16. The method of claim 12 wherein said alcohol is 1-butanol.

17. The method of claim 12 wherein said alcohol is 1-hexanol.

18. The method of claim 12 wherein said alcohol is 2-ethylhexanol.

19. The method of claim 12 wherein the alcohol is methanol.

20. The method of claim 12 wherein the mineral acid is hydrogen chloride.

21. The method of claim 12 wherein the hydrogenation catalyst is selected from the group consisting of palladium, platinum, nickel, rhenium, rhodium, ruthenium, and copper chromite.

22. The method of claim 21 wherein the hydrogenation catalyst is palladium.

* * * * *